(12) United States Patent
Khokhlova et al.

(10) Patent No.: US 12,157,018 B2
(45) Date of Patent: Dec. 3, 2024

(54) BOILING HISTOTRIPSY METHODS AND SYSTEMS FOR UNIFORM VOLUMETRIC ABLATION OF AN OBJECT BY HIGH-INTENSITY FOCUSED ULTRASOUND WAVES WITH SHOCKS

(71) Applicants: University of Washington, Seattle, WA (US); KONINKLIJKE PHILIPS N.V., A CORPORPORATION ORGANIZED AND EXISTING UNDER THE LAWS OF KINGDOM OF THE NETHERLANDS, Eindhoven (NL)

(72) Inventors: Vera Khokhlova, Seattle, WA (US); Michael R. Bailey, Seattle, WA (US); Navid Farr, Seattle, WA (US); Tatiana D. Khokhlova, Seattle, WA (US); Wayne Kreider, Seattle, WA (US); Adam D. Maxwell, Seattle, WA (US); Ari Partanen, Andover, MA (US); Oleg A. Sapozhnikov, Seattle, WA (US); George R. Schade, Seattle, WA (US); Yak-Nam Wang, Seattle, WA (US)

(73) Assignees: University of Washington, Seattle, WA (US); KONINKLIJKE PHILIPS N.V., A CORPORPORATION ORGANIZED AND EXISTING UNDER THE LAWS OF KINGDOM OF THE NETHERLANDS, Eindhoven (NL)

( * ) Notice: Subject to any disclaimer, the term of this patent is extended or adjusted under 35 U.S.C. 154(b) by 213 days.

(21) Appl. No.: 16/712,680

(22) Filed: Dec. 12, 2019

(65) Prior Publication Data
US 2020/0222728 A1  Jul. 16, 2020

Related U.S. Application Data

(63) Continuation of application No. 15/120,300, filed as application No. PCT/US2015/023069 on Mar. 27, 2015, now abandoned.
(Continued)

(51) Int. Cl.
*A61N 7/02* (2006.01)
*A61B 17/22* (2006.01)

(52) U.S. Cl.
CPC .......... *A61N 7/02* (2013.01); *A61B 17/22004* (2013.01); *A61B 2017/22007* (2013.01)

(58) Field of Classification Search
CPC ........................... A61N 7/02; A61B 17/22004
See application file for complete search history.

(56) References Cited

U.S. PATENT DOCUMENTS 5,485,839 A * 1/1996 Aida ...................... G01R 33/28
601/4
5,762,066 A 6/1998 Law et al.
(Continued)

FOREIGN PATENT DOCUMENTS

WO  2013/153506 A1  10/2013
WO  2015/148938 A2  10/2015

OTHER PUBLICATIONS

Khokhlova, et al., "Controlled tissue emulsification produced by high intensity focused ultrasound shock waves and millisecond boiling," J. Acoust. Soc. Am., vol. 130, No. 5, Pt. 2, pp. 3498-3510, 2011.
(Continued)

*Primary Examiner* — Daniel W Fowler
(74) *Attorney, Agent, or Firm* — McDonnell Boehnen Hulbert & Berghoff LLP

(57) ABSTRACT

An example method includes generating an acoustic ultrasound wave that is focused at a focal point. The method
(Continued)

further includes sequentially directing the focal point upon distinct portions of an object to form respective shock waves at the distinct portions of the object. The method further includes, via the respective shock waves, causing the distinct portions of the object to boil and form respective vapor cavities. The method further includes causing substantially uniform ablation of a region of the object that comprises the distinct portions. The substantially uniform ablation is caused via interaction of the respective shock waves with the respective vapor cavities. An example ablation system and an example non-transitory computer-readable medium, both related to the example method, are also disclosed.

21 Claims, 15 Drawing Sheets

Related U.S. Application Data

(60) Provisional application No. 61/972,035, filed on Mar. 28, 2014.

(56) References Cited

U.S. PATENT DOCUMENTS

| | | | |
|---|---|---|---|
| 6,501,978 B2 | 12/2002 | Wagshul et al. | |
| 6,516,211 B1 | 2/2003 | Acker et al. | |
| 6,542,767 B1 | 4/2003 | McNichols et al. | |
| 7,246,939 B1 | 7/2007 | Gultekin | |
| 2003/0233045 A1 | 12/2003 | Vaezy et al. | |
| 2004/0242999 A1 | 12/2004 | Vitek et al. | |
| 2006/0122509 A1* | 6/2006 | Desilets | A61N 7/02 601/2 |
| 2008/0146912 A1 | 6/2008 | Richard | |
| 2008/0221649 A1* | 9/2008 | Echague | A61B 18/203 607/100 |
| 2009/0143676 A1 | 6/2009 | Matsumura | |
| 2010/0094178 A1 | 4/2010 | Lacoste | |
| 2010/0125192 A1 | 5/2010 | Chopra et al. | |
| 2010/0179414 A1 | 7/2010 | Kuhn et al. | |
| 2010/0191157 A1 | 7/2010 | Sanghvi | |
| 2010/0210976 A1* | 8/2010 | Darlington | A61N 7/02 601/2 |
| 2010/0228122 A1 | 9/2010 | Keenan et al. | |
| 2011/0054315 A1 | 3/2011 | Roberts et al. | |
| 2011/0251528 A1* | 10/2011 | Canney | A61N 7/02 601/3 |
| 2011/0257523 A1 | 10/2011 | Hastings | |
| 2011/0282268 A1 | 11/2011 | Baker et al. | |
| 2012/0035464 A1 | 2/2012 | Raju et al. | |
| 2012/0116221 A1 | 5/2012 | Sehgal et al. | |
| 2012/0259250 A1 | 10/2012 | Sapozhnikov et al. | |
| 2012/0302927 A1 | 11/2012 | Khokhlova et al. | |
| 2013/0018260 A1 | 1/2013 | Sanghvi et al. | |
| 2013/0023862 A1 | 1/2013 | Marrouche et al. | |
| 2013/0041249 A1 | 2/2013 | Salomir et al. | |
| 2013/0102932 A1 | 4/2013 | Cain et al. | |
| 2013/0158387 A1 | 6/2013 | Tanttu | |
| 2013/0225994 A1 | 8/2013 | Hsu et al. | |
| 2013/0282040 A1 | 10/2013 | Jun | |
| 2013/0317360 A1 | 11/2013 | Hor et al. | |
| 2013/0345562 A1 | 12/2013 | Barthe et al. | |
| 2014/0024922 A1 | 1/2014 | Vijayvergia et al. | |
| 2014/0058294 A1 | 2/2014 | Gross et al. | |
| 2014/0277032 A1 | 9/2014 | Ahn et al. | |
| 2014/0316269 A1 | 10/2014 | Zhang et al. | |
| 2014/0330175 A1* | 11/2014 | Carol | A61N 7/022 601/2 |
| 2014/0350439 A1 | 11/2014 | Zur et al. | |
| 2015/0119763 A1 | 4/2015 | Canney et al. | |
| 2015/0359603 A1 | 12/2015 | Levy et al. | |
| 2017/0348040 A1 | 12/2017 | Govari et al. | |

OTHER PUBLICATIONS

Khokhlova, et al., "Design of HIFU transducers to generate specific nonlinear ultrasound fields," pp. 1-6, Physics Procedia, 2016.

Khokhlova, et al., "Ultrasound-guided tissue fractionation by high intensity focused ultrasound in an in vivo porcine liver model," Proceedings of the National Academy of Sciences, vol. 111, No. 22, pp. 8161-8166, 2014.

Kreider, et al., "Rectified growth of histotripsy bubbles," Proceedings of Meetings on Acoustics, vol. 19, 4 pages, 2013.

Kreider, et al., "Characterization of a Multi-Element Clinical HIFU System Using Acoustic Holography and Nonlinear Modeling," IEEE Transactions on Ultrasonics, Ferroelectrics, and Frequency Control, vol. 60, No. 8, pp. 1683-1698, 2013.

Maxwell, et al., "Disintegration of Tissue Using High Intensity Focused Ultrasound: Two Approaches That Utilize Shock Waves," Acoustics Today, pp. 24-37, 2012.

Maxwell, et al., "A Prototype Therapy System for Transcutaneous Application of Boiling Histotripsy," IEEE Transactions on Ultrasonics, Ferroelectrics, and Frequency Control, 15 pages, 2016.

Maxwell, et al., "Probability of Cavitation for Single Ultrasound Pulses Applied to Tissues and Tissue-Mimicking Materials," Ultrasound in Med. & Biol., vol. 39, No. 3, pp. 449-465, 2013.

PCT/US2015/023069 filed Mar. 27, 2015, Search Report and Written Opinion, 13 pages, 2015.

Picone, "Separatory Magnetic Transport (SMT) in Magnetic Resonance Force Microscopy: Theory & Experiment," University of Washington Department of Medical Engineering and Department of Orthopaedics, 15 pages, 2012.

Simon, et al., "2aBA9. Ultrasonic atomization: A mechanism of tissue fractionation," Proceedings of Meetings on Acoustics, vol. 19, 4 pages, 2013.

Simon, et al., "Investigation Into the Mechanisms of Tissue Atomization by High-Intensity Focused Ultrasound," Ultrasound in Med. & Biol., vol. 41, No. 5, pp. 1372-1385, 2015.

Simon, et al., "Tissue Atomization by High Intensity Focused Ultrasound," IEEE International Ultrasonics Symposium Proceedings, pp. 1003-1006, 2012.

Simon, et al., "Ultrasonic atomization of liquids in drop-chain acoustic fountains," J Fluid Mech., vol. 766, pp. 12-146, 2015.

Simon, et al., "Ultrasonic atomization of tissue and its role in tissue fractionation by high intensity focused ultrasound," Physics in Medicine and Biology., vol. 57, pp. 8061-8078, 212.

Wang, et al., "Biomedical Acoustics Session 3aBAb: Generation and Detection of High Intensity Focused Ultrasound Lesions," Proceedings of Meetings on Acoustics, vol. 19, 3 pages, 2013.

Wang, et al., "Histological and Biochemical Analysis of Mechanical and Thermal Bioeffects in Boiling Histotripsy Lesions Induced by High Intensity Focused Ultrasound," Ultrasound in Medicine & Biology, vol. 39, No. 3, pp. 424-438, 2013.

Yuldashev, et al., "Characterization of nonlinear ultrasound fields of 2D therapeutic arrays," IEEE International Ultrasonics Symposium Proceedings, pp. 925-928, 2012.

Canney, et al., "Shock-induced heating and millisecond boiling in gels and tissue due to high intensity focused ultrasound," Ultrasound Med. Biol., vol. 36, No. 2, pp. 250-267, 2010.

Damianou, et al., "MRI monitoring of lesions created at temperature below the boiling point and of lesions created above the boiling point using high intensity focused ultrasound," Journal of Biomedical Science and Engineering, pp. 764-765, 767, 2010.

Kim, et al., Volumetric MRI-HIFU ablation of uterine fibroids: role of treatment cell size in the improvement of energy efficiency, Eur J Radiol, vol. Nov. 81, No. 11, pp. 3652-3659, 2012.

Kohler, et al., "Volumetric HIFU ablation under 3D guidance of rapid MRI thermometry," Med Phys., vol. 2009, vol. 36, No. 8, pp. 3521-3535, 2009.

PCT/US15/23021 International Search Report and Written Opinion of the International Searching Authority, 30 pages, mailing date Sep. 29, 2015.

Khokhlova et al., "Stimulated Release of Nucleic Acid Cancer Biomarkers by Hifu: A Study in a Rat Prostate Cancer Model", Stimulated Release, Campus of SITU Shanghai, 2013, 1 page.

(56) References Cited

OTHER PUBLICATIONS

Keshavarzi et al., "Treatment of uterine fibroid tumors in an in situ rat model using high-intensity focused ultrasound", Fertility and Sterility, 2003, 80(2), 761-767.
Khokhlova et al., "HIFU for palliative treatment of pancreatic cancer", Journal of Gastrointestinal Oncology, 2011, 2(3), 175-184.
Vlaisavljevich, E et al. "Image-guided non-invasive ultrasound liver ablation using histotripsy: Feasibility study in an in vivo porcine model." Ultrasound in medicine & biology 39.8 2013): 1398-1409. Aug. 31, 2013.
Bebbington, M et al. "Comparison of ultrasound and magnetic resonance imaging parameters in predicting survival in isolated left-sided congenital diaphragmatic hernia." Ultrasound in Obstetrics & Gynecology 43.6 (2014): 670-674. May 5, 2014; p. 670.
International Search Report PCT/US16/38052, mailed Sep. 8, 2016.

\* cited by examiner

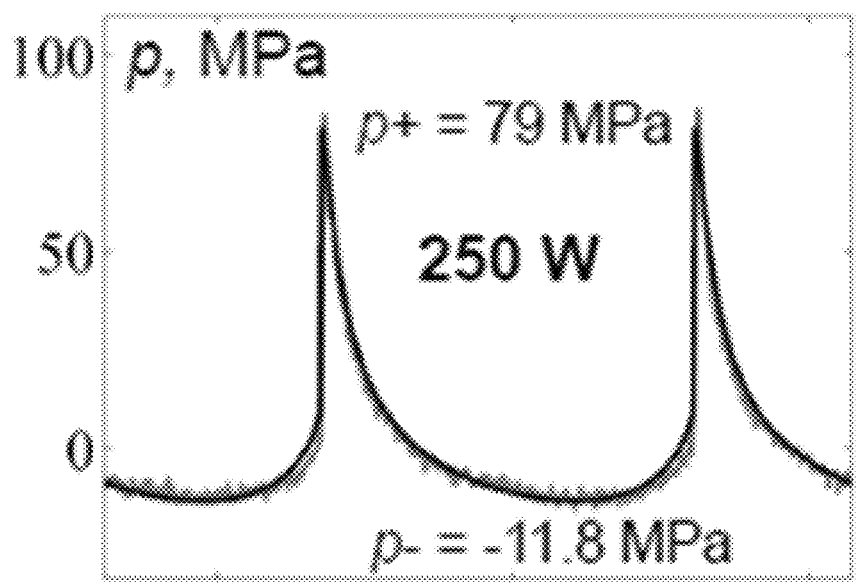
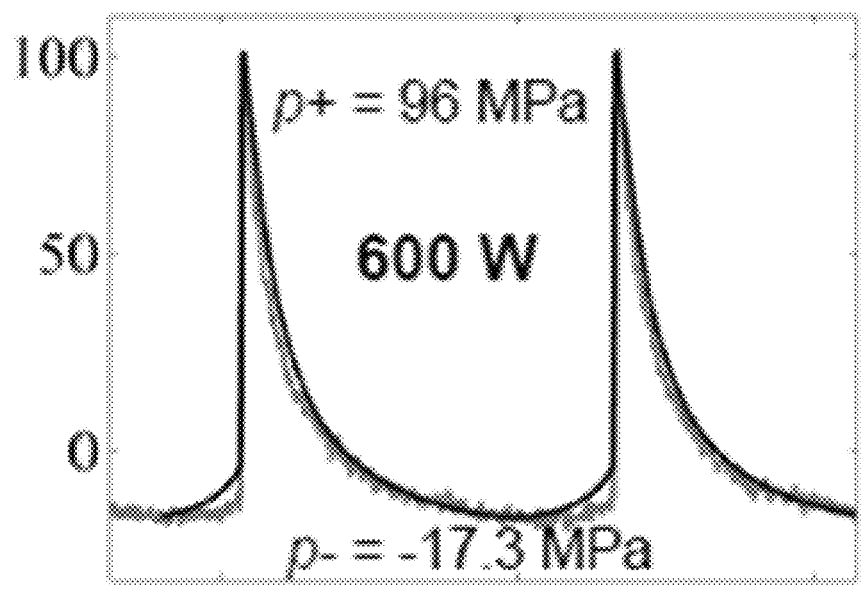
FIG. 6

FIG. 7

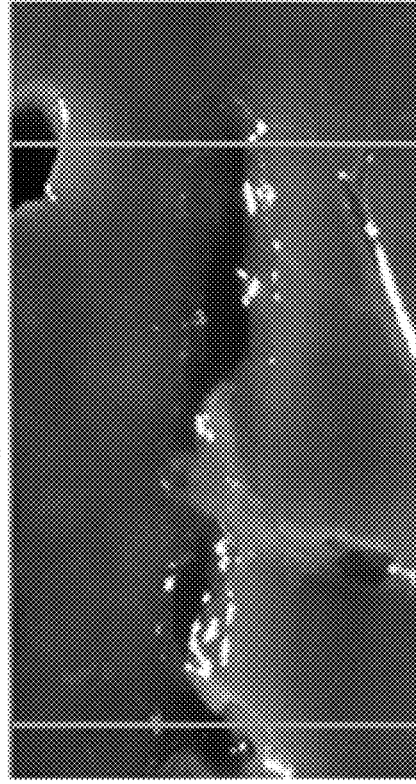
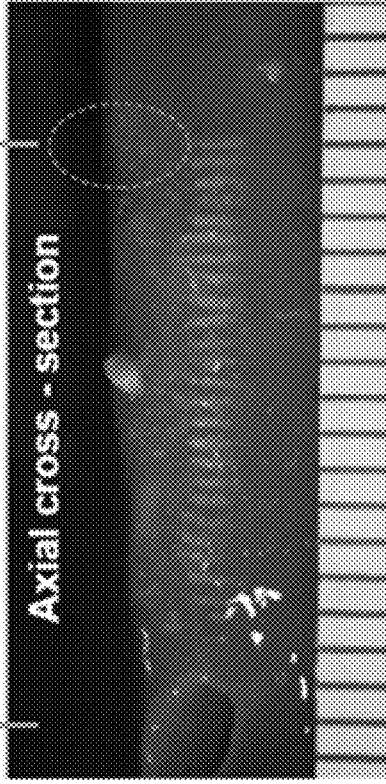
FIG. 9

Connective tissue *versus* liver tissue in boiling histotripsy lesion

Examples: 250 W peak power, different duty factor 1 cm diameter lesion
2 circles, 30 pulses per point, 25 points,
2 layers 5 mm apart
cross-section, top

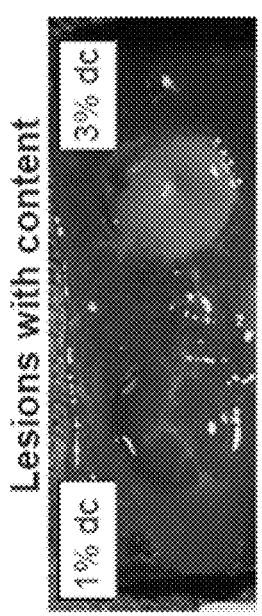

Lesions with content

1% dc    3% dc

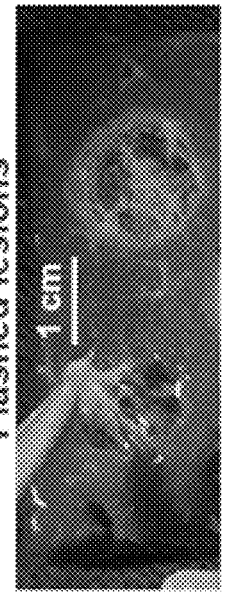

Flashed lesions 1 cm 2 cm diameter lesion
4 circles, 25 pulses per point, 81 points Lesion with content

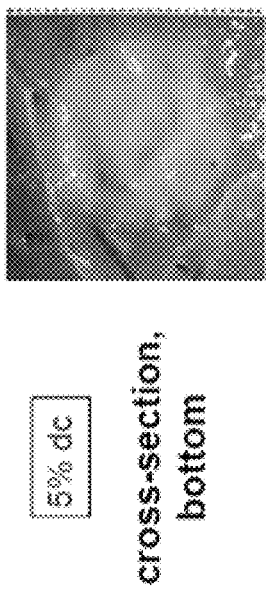

5% dc
cross-section, bottom

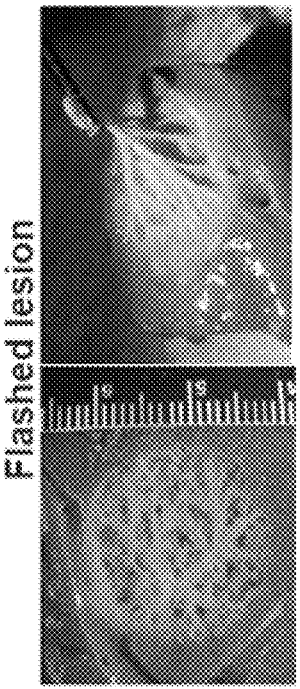

Flashed lesion

Vessels (connective tissue) are more resistant to BH than liver tissue

FIG. 11

BOILING HISTOTRIPSY METHODS AND SYSTEMS FOR UNIFORM VOLUMETRIC ABLATION OF AN OBJECT BY HIGH-INTENSITY FOCUSED ULTRASOUND WAVES WITH SHOCKS

CROSS-REFERENCE TO RELATED APPLICATION

This application is a continuation of U.S. patent application Ser. No. 15/120,300, filed on Aug. 19, 2016, which is a U.S. national phase of International Application No. PCT/US2015/023069, filed on Mar. 27, 2015, which claims priority to U.S. Provisional Patent Application No. 61/972,035, filed Mar. 28, 2014, the contents of which are all incorporated herein by reference in their entirety.

STATEMENT REGARDING FEDERALLY SPONSORED RESEARCH OR DEVELOPMENT

This invention was made with government support under grant nos. K01 EB015745-01, R01 EB007643-05, and T32 DK007779-12, awarded by the National Institutes of Health, and grant no. SMST03402, awarded by the National Space Biomedical Research Institute. The government has certain rights in the invention.

BACKGROUND

Unless otherwise indicated herein, the materials described in this section are not prior art to the claims in this application and are not admitted to be prior art by inclusion in this section.

High-intensity focused ultrasound (HIFU) boiling histotripsy (BH) methods use pulsed HIFU waves with shock fronts to mechanically ablate an object at a focal point of the pulsed wave by rapidly inducing boiling within the object. Mechanical ablation of the object occurs via interaction of shock fronts with a vapor cavity created within the object by the BH induced boiling. Current methods for HIFU boiling histotripsy are limited to ablation of portions of an object that are comparable in size to the focal point of the HIFU wave.

SUMMARY

An example method includes generating an acoustic ultrasound wave that is focused at a focal point. The method further includes sequentially directing the focal point upon distinct portions of an object to form respective shock waves at the distinct portions of the object. The method further includes, via the respective shock waves, causing the distinct portions of the object to boil and form respective vapor cavities. The method further includes causing substantially uniform ablation of a region of the object that comprises the distinct portions. The substantially uniform ablation is caused via interaction of the respective shock waves with the respective vapor cavities.

An example non-transitory computer-readable medium storing instructions, that when executed by an ablation system, cause the ablation system to perform functions. The functions include generating an acoustic ultrasound wave that is focused at a focal point. The functions further include sequentially directing the focal point upon distinct portions of an object to form respective shock waves at the distinct portions of the object. The functions further include, via the respective shock waves, causing the distinct portions of the object to boil and form respective vapor cavities. The functions further include causing substantially uniform ablation of a region of the object that comprises the distinct portions. The substantially uniform ablation is caused via interaction of the respective shock waves with the respective vapor cavities.

An example ablation system is configured to ablate an object. The ablation system includes one or more processors; a sensor module configured to collect sensory data from the object during ablation; an input/output interface configured to receive user input and display an image representing the sensory data; an ablation module configured to generate an acoustic ultrasound wave and sequentially direct a focal point of the acoustic ultrasound wave upon distinct portions of the object; and a non-transitory computer-readable medium storing instructions that, when executed by the one or more processors, cause the ablation system to cause substantially uniform ablation of a region of the object that comprises the distinct portions.

When the term "substantially" or "about" is used herein, it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide. In some examples disclosed herein, "substantially" or "about" means within +/−5% of the recited value. In other instances, "substantially uniform ablation of a region of the object" may mean that the region is ablated with a high degree of uniformity useful in treating a human subject having the undesirable object within their body.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 6 depicts pressure waveforms with shocks generated at a focus within a test medium.

FIG. 7 depicts example ablation trajectories of a focus of a shock wave within a test medium.

FIG. 9 depicts additional ablated lines in ex-vivo bovine liver tissue.

FIG. 11 depicts ablation of ex-vivo liver tissue.

DETAILED DESCRIPTION

Figure 1:
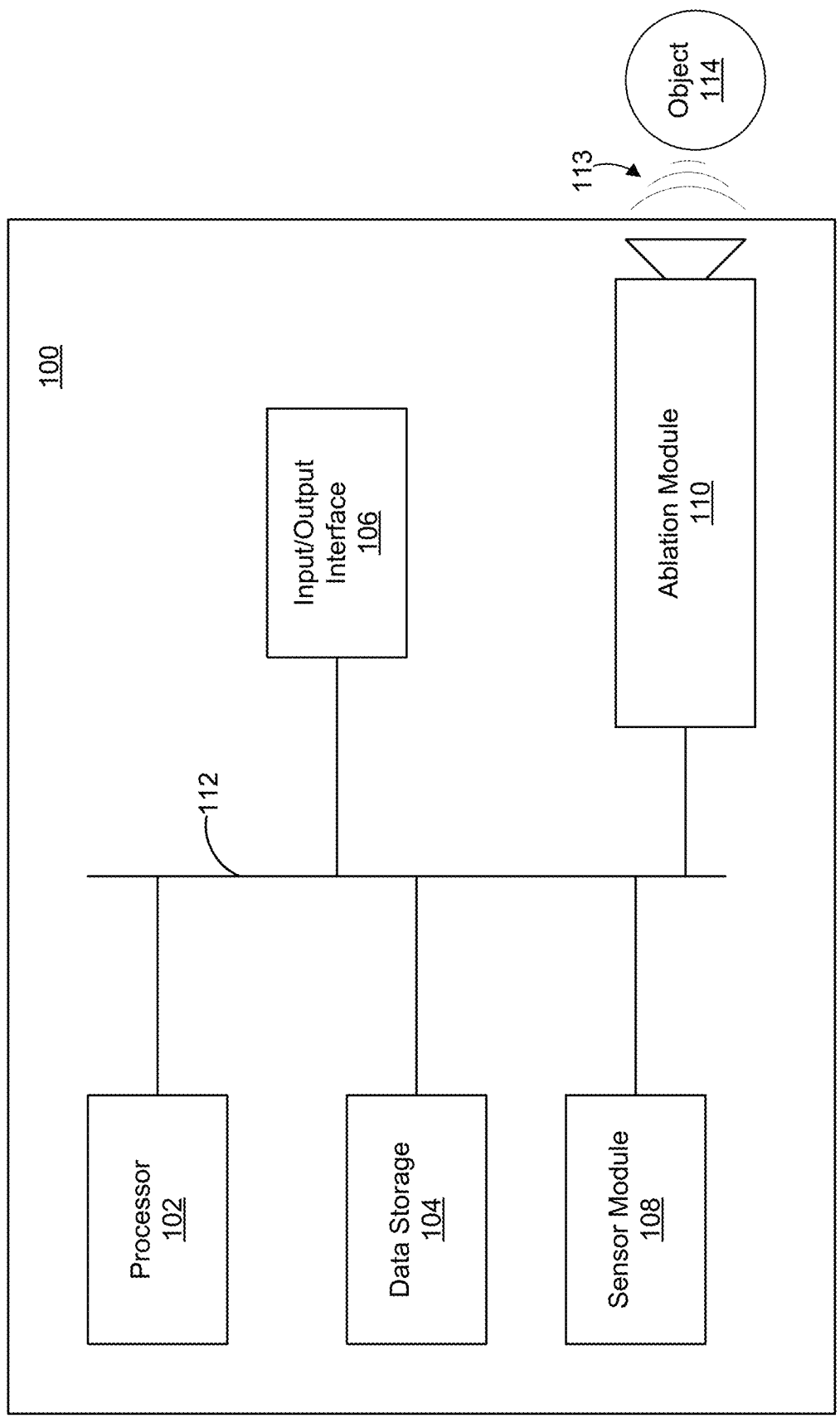
FIG. 1 illustrates an example ablation system configured to ablate an object.

A HIFU wave having a power density of less than 1 kW/cm$^2$ can be sequentially focused upon various portions of an object so that a relatively large region of the object is thermally ablated. HIFU boiling histotripsy (BH) utilizing pulsed HIFU waves having power density of at least 10 kW/cm$^2$ is also useful for mechanical ablation of small portions of an object, but has previously not been used to mechanically ablate regions that are substantially larger than a focal point of the HIFU wave. These currently known HIFU methods for thermal or mechanical ablation suffer from disadvantages that are discussed below.

Using HIFU waves to predictably and uniformly thermally ablate a relatively large region of an object may require process downtime between ablation of successive smaller portions of the object. The process downtime allows a most recently ablated portion of the object to cool before ablation of a successive portion begins. If portions of the object are heated without allowing other recently heated portions to cool, the portion absorbing the HIFU wave and/or surrounding portions may overheat. Causing thermal ablation of successive portions of the object without allowing for cooling may introduce non-uniformity and unpredictability to the ablation process and to the final ablated tissue volume. In this way, thermal ablation using HIFU waves exhibits a "memory effect."

More specifically, uniform thermal ablation of two portions of an object generally requires that the two portions experience the same absorbed HIFU power for the same continuous duration, starting from the same initial temperature. This combination of absorbed HIFU power, exposure time, and initial temperature is sometimes referred to as a HIFU "thermal dose." However, if the two portions are adjacent, heat generated in ablating the first portion may diffuse into the second portion, raising the temperature of the second portion before the second portion receives its predetermined HIFU dose. This will generally cause the second portion to absorb more heat than the first portion, unless the HIFU thermal dose for the second portion is appropriately compensated. However, it is difficult to accurately determine how much surplus heat the second portion absorbs while the first portion is being ablated. Therefore, it is usually desirable to give each portion of the object an equal "thermal dose" of the HIFU wave, while allowing time for sufficient cooling between ablating each portion. The process downtime represented by such cooling time periods makes the thermal ablation process somewhat inefficient.

The effectiveness of HIFU boiling histotripsy in uniformly mechanically ablating a relatively large region of an object has been previously unknown. As shown in this disclosure, uniform mechanical ablation of a large region of an object will generally include various smaller portions of the object each receiving a uniform HIFU "BH dose" consisting of a given number of HIFU pulses of a given shock amplitude, pulse duration, oscillation frequency, and duty cycle. In some examples, the various portions may each respectively receive the uniform HIFU BH dose comprising a given number of HIFU pulses in one continuous ablation session. In other examples, a first portion of the object may receive some of the given number of HIFU pulses, then a second portion of the object may receive one or more HIFU pulses, then the first portion may receive the remainder of the given number of pulses.

In contrast to thermal ablation methods, uniform mechanical ablation of two portions of an object does not require that the two portions receive the given number of HIFU pulses within the same duration of time. The methods disclosed herein exhibit uniform mechanical ablation of a relatively large region of an object without the need for process downtime related to cooling. HIFU intensities used in the disclosed methods are high enough to generate shock waves at or near the focal point of the HIFU wave. The shock waves then cause a portion of the object to boil, which in turn generates a vapor cavity. Subsequent shock waves interact with a vapor cavity within each portion of the object to cause mechanical ablation of the portion of the object after a certain number of pulses. Unexpectedly, the disclosed methods have advantages that differ from previously known methods in the following ways.

First, uniform ablation of two portions of an object no longer requires that the two portions receive a given number of pulses over the same amount of time. Using the disclosed methods, two portions can be uniformly ablated even though the two portions receive HIFU pulses that differ in continuity. For example, uniform ablation of first and second portions may result from the first portion receiving a dose of 30 pulses of 100 MPa shock amplitude, 10 ms pulse duration, and 1 Hz repetition frequency, and then the second portion receiving the same dose. In another example, uniform ablation of the first and second portions could result from the first and second portions alternately receiving pulses that are generated with the same shock wave amplitude, pulse duration and pulse repetition frequency. Because the disclosed methods are primarily mechanical and not thermal processes, temperature history of each portion and the way each portion accumulates the required dose (number of pulses), sequentially or alternatively, are largely irrelevant in this context.

On a related note, the primarily mechanical nature of the disclosed methods means that ablation of a first portion generally has little effect on a second portion. Short bursts of HIFU waves having a shock amplitude of at least 40 MPa have been shown to generally affect only the portion of the object impacted by the HIFU wave and not surrounding portions.

Referring now to the Figures, FIG. 1 illustrates an example ablation system 100 configured to ablate an object 114 using an acoustic ultrasound wave (or "HIFU" wave) 113. The ablation system 100 may include a processor 102, data storage 104, an input/output interface 106, a sensor module 108, and an ablation module 110, any or all of which may be communicatively coupled to each other via a system bus or another connection mechanism 112.

The processor 102 may include a general purpose processor and/or a special purpose processor and may be configured to execute program instructions stored within data storage 104. In some examples, the processor 102 may be a multi-core processor comprised of one or more processing units configured to coordinate to execute instructions stored within data storage 104. In one example, the processor 102, by executing program instructions stored within data storage 104, may provide HIFU parameters to the ablation module 110 for generation and/or directional focusing of HIFU waves. In another example, the processor 102 may provide HIFU parameters that are received via the input/output interface 106 to the ablation module 110.

Data storage 104 may include one or more volatile, non-volatile, removable, and/or non-removable storage components. Data storage 104 may be a magnetic, optical, or flash storage medium, and may be integrated in whole or in part with the processor 102 or other portions of the ablation system 100. Further, the data storage 104 may be a non-transitory computer-readable storage medium, having stored thereon program instructions that, when executed by the processor 102, cause the ablation system 100 to perform one or more functions described in this disclosure. Such program instructions may be part of a software application that can be executed in response to inputs received from the input/output interface 106, for instance. The data storage 104 may also store other types of information or data, such as those types described throughout this disclosure.

The input/output interface 106 may enable interaction with a user of the ablation system 100, if applicable. The input/output interface 106 may include input components such as dials, buttons, a keyboard, a mouse, a keypad, or a touch-sensitive panel, and output components such as a display screen (which, for example, may be combined with a touch-sensitive panel), a sound speaker, and a haptic feedback system. In one example, the input/output interface 106 may receive input indicating (i) various parameters defining a HIFU wave to be generated by the ablation module 110 and/or (ii) various parameters for sequentially directing the focal point of the HIFU wave upon various portions of the object 114.

In some examples, the input/output interface 106 may include a display screen for displaying images of the object 114 or other sensory data collected by the sensor module 108. Properly determining a trajectory for ablating the object 114 will generally require characterizing the size, shape, location, and/or consistency of the object 114. The display screen may display images of the object 114 that are captured by the sensor module 108. The displayed images of the object 114 may be used prior to ablation to determine a suitable ablation trajectory, or could be used in a real-time manner by monitoring ablation progress of the object 114 and adjusting the ablation trajectory accordingly.

The sensor module 108 may include any known hardware and/or software configured to collect sensory data from the object 114 during ablation. For example, the sensor module 108 may include an imaging system to capture an image of the object 114 and provide the captured image to the input/output interface 106 for display. For example, the sensor module 108 may include an ultrasound transducer configured to (i) generate ultrasound waves that are scattered and/or reflected by the object 114, (ii) detect the ultrasound waves reflected and/or scattered by the object 114, and (iii) generate an image of the object 114 using the detected ultrasound waves. In another example, the sensor module 108 may include a magnetic resonance imaging (MRI) system. Any known imaging technique capable of imaging an object located within a human subject is contemplated herein.

The sensor module 108 may further include a voltage probe and/or an oscilloscope used to monitor the drive voltage of a transducer of the ablation module 110, which can be indicative of whether boiling is occurring within the object 114. This feedback can be used to tune HIFU wave parameters such as pulse duration, oscillation frequency, power, or duty cycle of the HIFU wave 113.

The sensor module 108 may further include a passive cavitation detector (PCD) which may be used to detect acoustic scattering caused by the HIFU wave 113 within the object 114. Such acoustic scattering may be indicative of boiling of the object 114. This feedback can similarly be used to tune parameters of the HIFU wave 113.

In some examples, the sensor module 108 may be integrated with the ablation module 110. For instance, a single ultrasound transducer or transducer array may be used for both HIFU ablation of the object 114 and ultrasound imaging of the object 114.

The ablation module 110 may include a signal generator configured to receive data from the processor 102 or input/output interface 106 that is representative of parameters for the HIFU wave 113. For instance, the processor 102 may send, to the ablation module 110, data representative of input received via the input/output interface 106. In another example, the received input may simply indicate one of several predetermined HIFU ablation protocols represented by program instructions stored at data storage 104. Such data received by the ablation module 110 may indicate various HIFU parameters such as operating power of the ablation module 110, power density of the HIFU wave 113, oscillation frequency of the HIFU wave 113, pulse duration of the HIFU wave 113, duty cycle of the HIFU wave 113, and a number of HIFU pulses to be generated for various portions of the object 114. The received data may also indicate a trajectory, path, or sequence of portions of the object 114 upon which the focal point of the HIFU wave 113 should be sequentially directed upon. In other examples, the path of the HIFU wave 113 may be manually and/or mechanically directed. The received data may also include timing information indicating when and/or for how long the focal point of the HIFU wave should be directed upon each respective portion of the object 114. In some examples, the ablation module 110 may include a signal amplifier used to generate the HIFU wave 113 at a desired power.

The ablation module 110 may include one or more piezoelectric transducer elements configured to generate HIFU waves in response to receiving respective control signals representing HIFU parameters. For example, the ablation module 110 may include a phased array of transducer elements configured to electronically focus or steer a generated HIFU wave upon various portions of the object 114 via constructive and/or destructive wave interference. Each transducer element of the ablation module 110 may receive its own independent control signal. The ablation module 110 may also include one or more of (i) a lens, (ii) one or more transducers having a radius of curvature at the focal point of the HIFU wave, and (iii) a phased array of transducers. The ablation module 110 may be configured to generate a HIFU wave of oscillation frequency ranging from 0.5-20 MHz, but other examples are possible.

The object 114 may include any object suitable for HIFU ablation. Some examples of an object 114 include biological tissue such as a liver tissue, a kidney tissue, a muscle tissue, a fat tissue, a brain tissue, a nerve tissue, a tumor, a hematoma, an abscess, a lipoma, or any other diseased or undesirable tissue. For instance, the object 114 may reside within a human subject.

Figure 2:
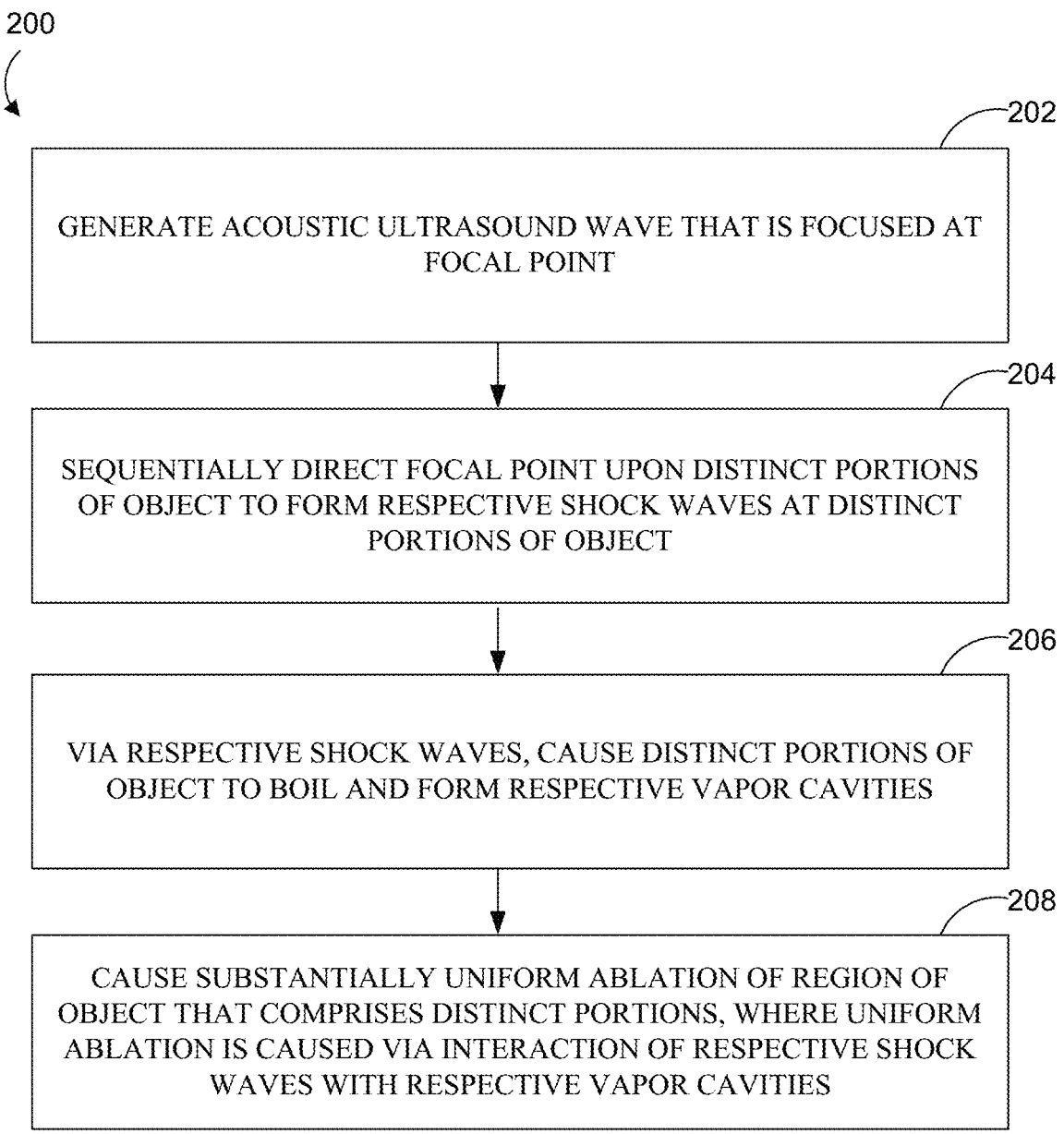
FIG. 2 is a flow chart depicting an example method.

FIG. 2 is a flow chart depicting an example method 200 for causing substantially uniform ablation of a region of an object that comprises distinct portions. At block 202, the method 200 involves generating an acoustic ultrasound wave that is focused at a focal point. Hereinafter, the acoustic ultrasound wave may also be referred to as the HIFU wave. In many examples, the HIFU wave may take the form of a pulsed HIFU wave.

The HIFU wave may be generated by ablation system 100 according to one or more parameters received via input/output interface 106 and/or stored at data storage 104. The HIFU wave may be focused at a focal point defined by the geometry of the ablation module 110, and/or focused electronically via providing appropriate respective control signals to a phased array of transducer elements of the ablation module 110. The HIFU wave may be generated by the ablation module 110 via one or more of a lens or one or more transducers having a radius of curvature at the focal point. The focal point of the HIFU wave may resemble a zero-dimensional point, or in other examples, the focal point may resemble a two-dimensional focal area or a three-dimensional focal volume.

Figure 3:
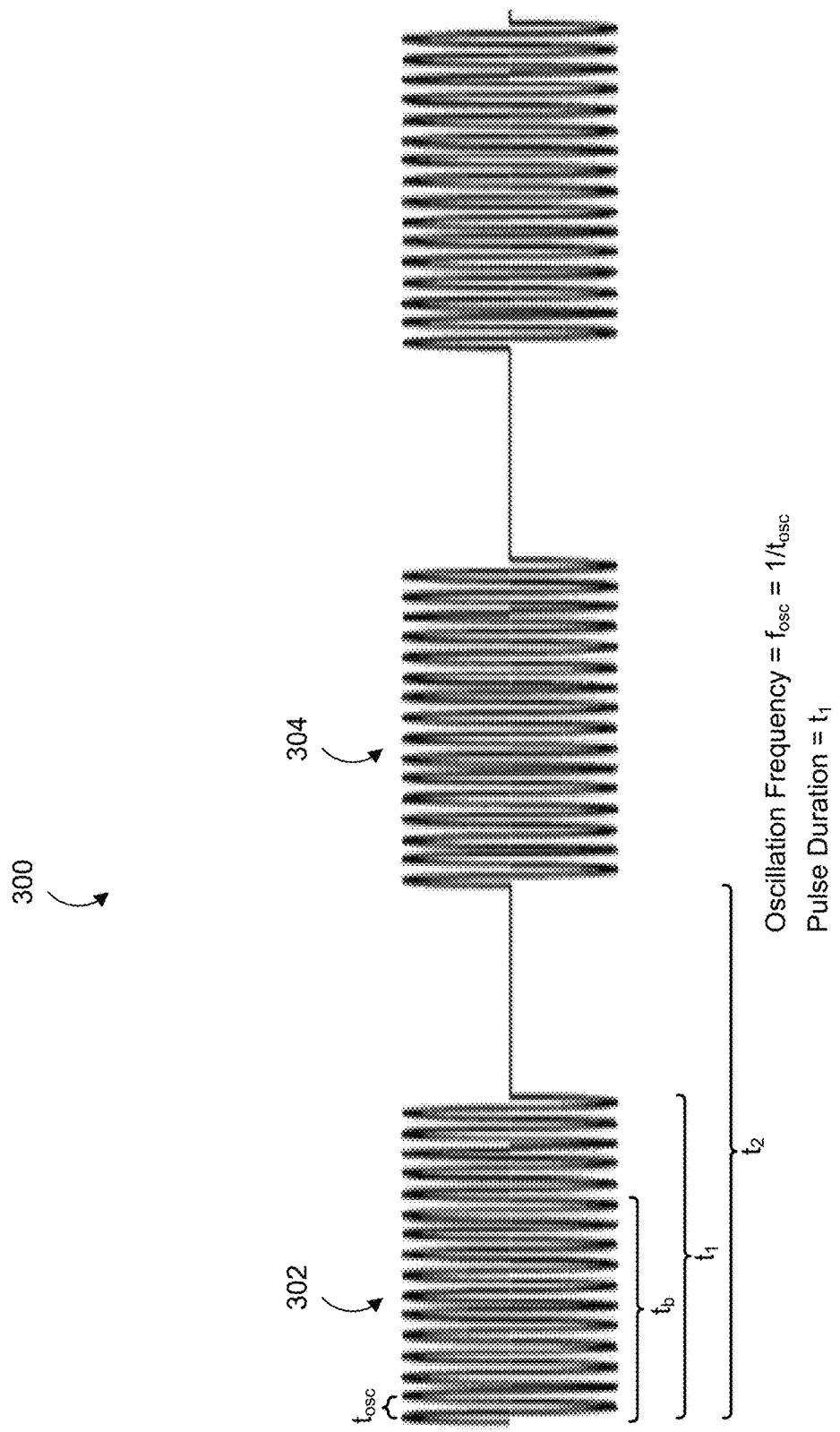
FIG. 3 depicts a waveform representing an example ultrasound wave generated by an ablation system.

Various HIFU wave parameters described below may be useful for causing substantially uniform ablation of a macroscopic region of an object. In some examples, the HIFU wave has an oscillation frequency that is greater than 900 kHz and less than 20 MHz. More specifically, the HIFU wave may have an oscillation frequency of about 1.2 MHz. Referring to FIG. 3 as an example, the HIFU wave 300 may exhibit an oscillation frequency $f_{osc}$=1.2 MHz that corresponds to an oscillation period of $t_{osc}$=0.833 µs.

In some examples, the HIFU wave 300 has a pulse duration $t_1$ that is greater than 0.1 millisecond (ms) and less than or equal to 40 ms. More specifically, the HIFU wave 300 may have a pulse duration that is greater than or equal to 1 ms and less than or equal to 20 ms, or about 10 ms. In another example, the pulse duration is within the range 1-10 ms. For example, the HIFU wave 300 may have a pulse duration of $t_1$=10 ms and a pulse repetition period of $t_2$=1 second, resulting in a duty cycle ($t_1/t_2$) of 1%. Note that with respect to any examples described herein, HIFU wave 300 might not be shown to scale in FIG. 3.

In some examples, the HIFU wave 300 has a pulse repetition frequency $f_2$ that corresponds to a pulse repetition period of $t_2$. The pulse repetition frequency $f_2$ may be within the range 0.5-15 Hz. More specifically, the HIFU wave 300 may have a pulse repetition frequency within the range 1-4 Hz. Certain embodiments include respective pulse repetition frequencies of 1 Hz and 4 Hz.

The HIFU wave 300 may also exhibit a duty cycle ($t_1/t_2$) that represents a ratio of the pulse duration $t_1$ over the pulse repetition period $t_2$. In some examples, the HIFU wave 300 has a duty cycle that is greater than 0.5% and less than 12%. More specifically, the HIFU wave 300 may have a duty cycle of about 1%. In other examples the HIFU wave 300 may have a duty cycle of 3%, 5%, or 10%. Such relatively short duty cycles may beneficially limit an amount of heat that accumulates within the object 114 during ablation.

In some examples, a given portion of the object receives a predetermined number of multiple consecutive pulses of the HIFU wave 300 to cause mechanical ablation, and then the HIFU wave 300 is directed to other portions of the object.

In other examples, a given portion of the object receives less than the predetermined amount of pulses, and then the HIFU wave is directed to other portions of the object. The process is then repeated until each portion receives the predetermined number of pulses to cause complete mechanical ablation. In such an example, such relatively low duty cycles (e.g., 1%-3%) might not be required because the given portion only receives a small number of pulses before the HIFU wave is directed elsewhere.

As discussed below, a HIFU wave defined by certain parameters may induce boiling of a given portion the object while the given portion absorbs a HIFU pulse. The pulse duration $t_1$ may advantageously be somewhat longer than a time-to-boil $t_b$ required to bring the given portion to a boil with the HIFU wave 300. Likewise, the duty cycle of the HIFU wave 300 may be low enough so that substantial amounts of heat do not accumulate and diffuse into surrounding portions of the object. In some examples, $t_b$ may be at least about 20% and no greater than about 80% of the pulse duration $t_1$. More specifically, $t_b$ may be about 50% of $t_1$.

The HIFU wave 300 may be generated by the ablation system 100 operating at an operating power ranging from 100-2000 W. More specifically, the operating power may be 250 W or may be 600 W. The operating power of the ablation system 100 may be defined as the amount of electrical power dissipated by the ablation module 110 when the HIFU wave 300 is generated.

At block 204, the method 200 involves sequentially directing the focal point upon distinct portions of an object to form respective shock waves at the distinct portions of the object. The object may include the object 114. In some examples, a shock wave formed at a portion of the object may have a shock amplitude of at least about 40 MPa at a focus of the shock wave. 40 MPa may be an approximate shock amplitude necessary to cause boiling within the object within a few milliseconds. In some examples, a shock wave formed at a given portion of the object may have a shock amplitude of at least about 50 MPa and no greater than 150 MPa.

In some examples, the focal point of the HIFU wave may be sequentially directed upon portions of the object that are each at least 1 millimeter (mm) wide and no greater than 5 mm wide. In further examples, the focal point of the HIFU wave may be sequentially directed upon portions of the object each having an area of at least 1 square millimeter (mm²) and no greater than 30 mm². More specifically, each portion may have an area of about 15 mm².

The focal point of the HIFU wave may be sequentially directed upon portions of the object that as a whole have a total length of at least 1 centimeter (cm), a total area of at least 1 square centimeter (cm²), and/or a total volume of at least 1 cubic centimeter (cm³). In this way, the focal point of the HIFU wave can be directed upon several relatively small portions of the object to ablate a larger macroscopic region of the object, as discussed further below.

Figure 4A:
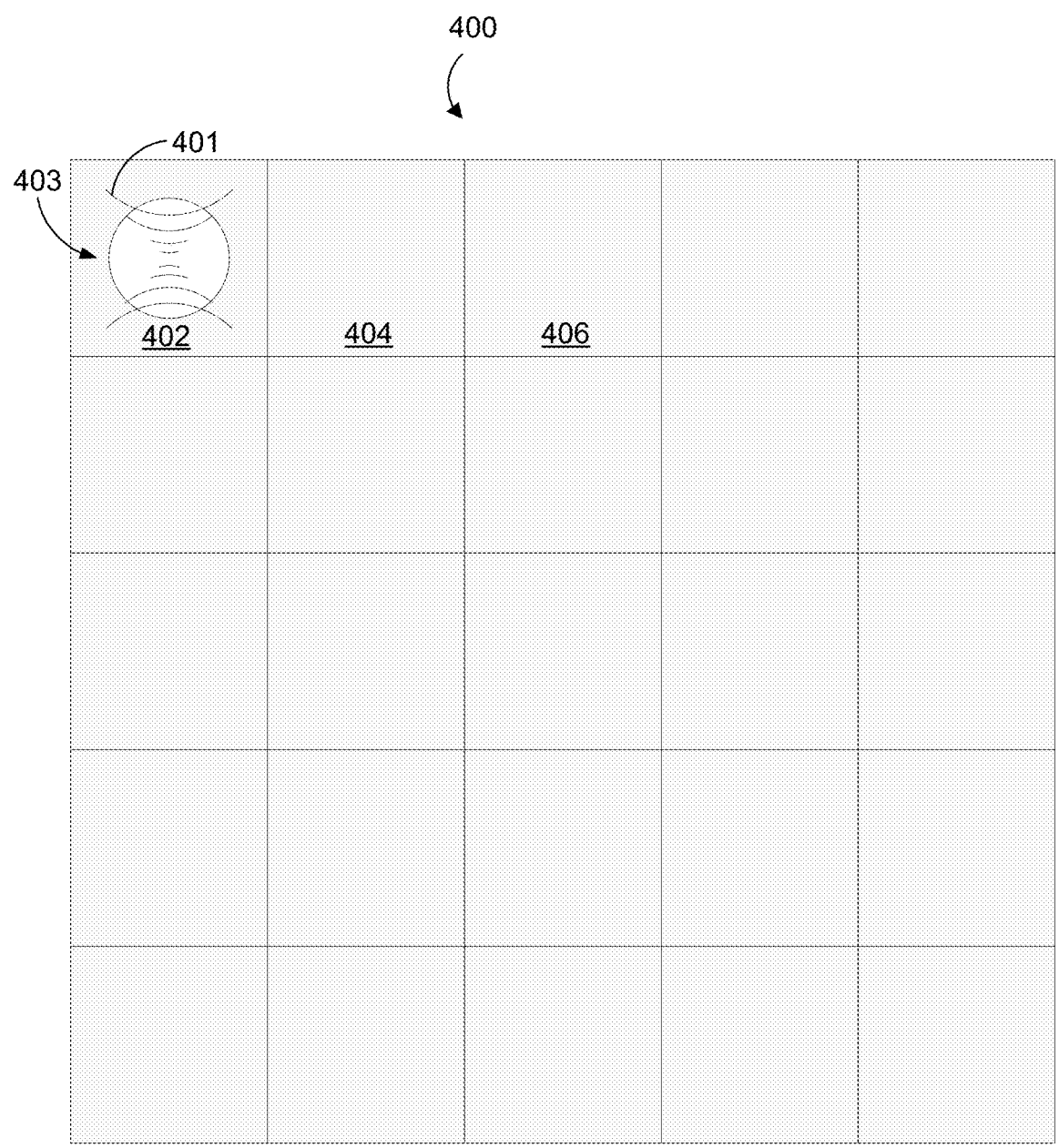
FIG. 4A depicts ablation of a first portion of an example object.
Figure 4B:
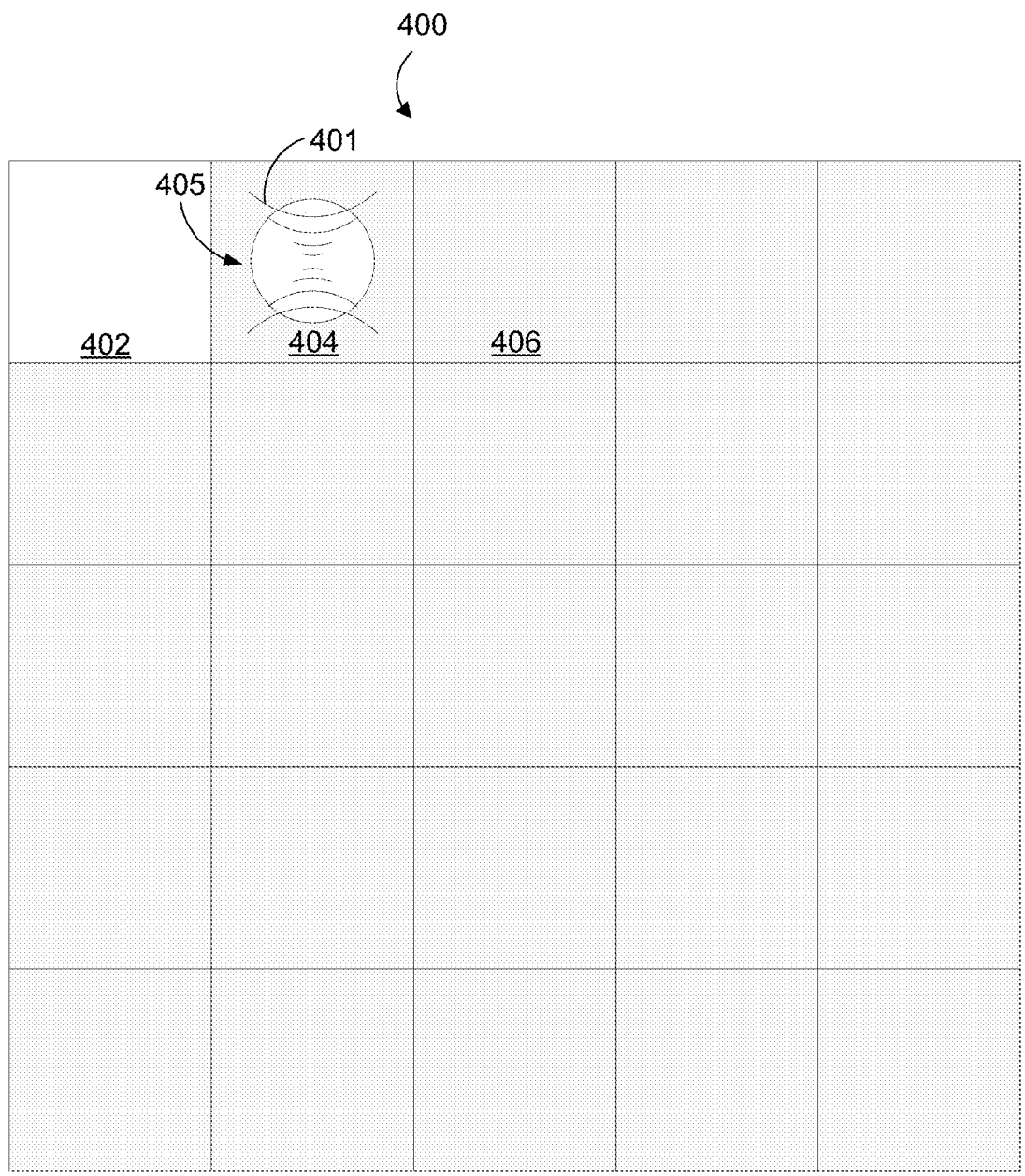
FIG. 4B depicts the ablated first portion of the example object and ablation of a second portion of the example object.
Figure 4C:
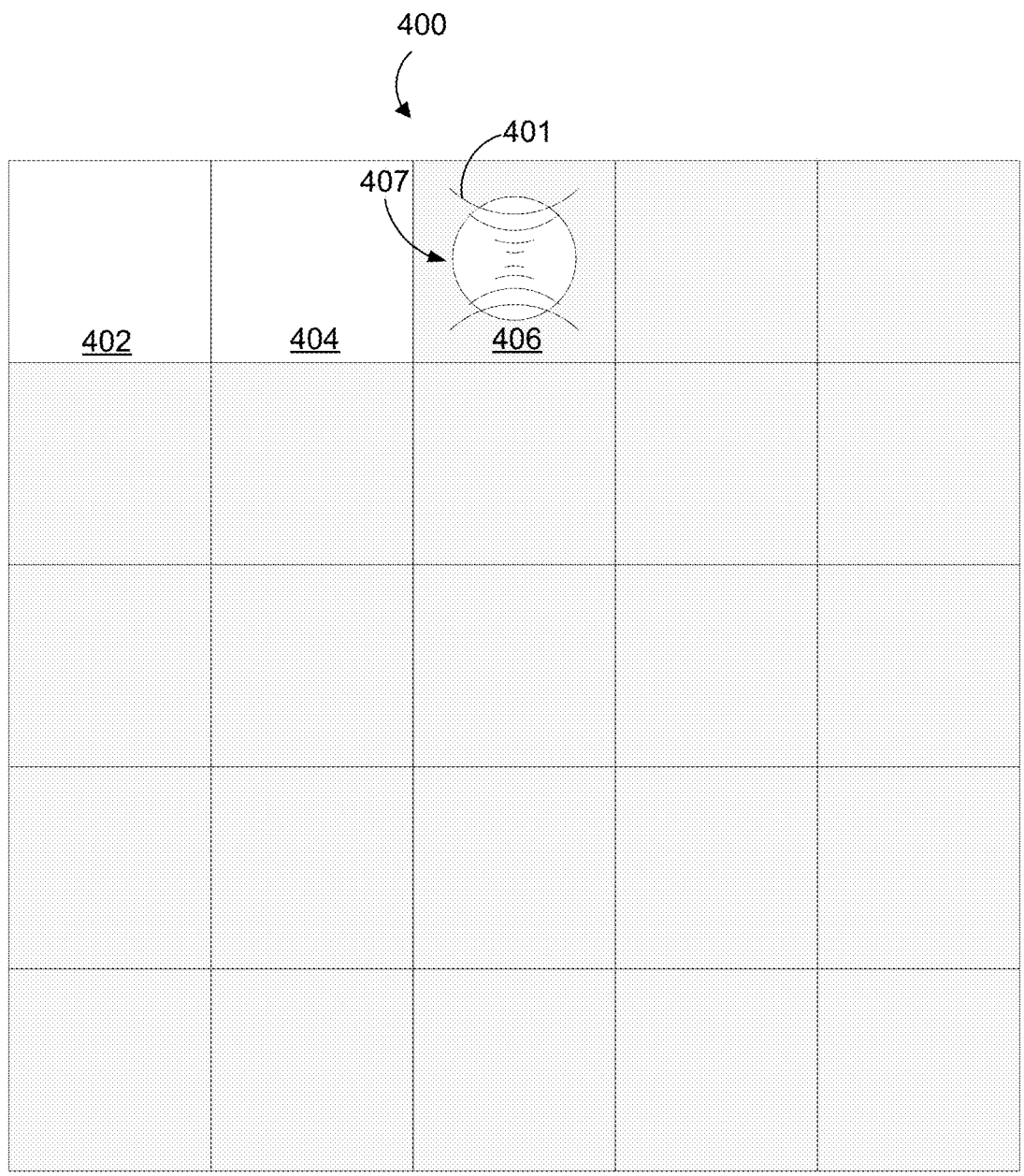
FIG. 4C depicts the first and second ablated portions of the example object and ablation of a third portion of the example object.

In one example, the focal point of the HIFU wave 401 may be sequentially focused first upon portion 402 of the object 400 as shown in FIG. 4A, then upon portion 404 of the object 400 as shown in FIG. 4B, and then upon portion 406 of the object 400 as shown in FIG. 4C. This may result in shock waves being sequentially formed at the portions 402, 404, and 406. Other example trajectories or sequences for direction of the focal point of the HIFU wave 401 along various portions of the object 400 are also possible. As the HIFU wave 401 is sequentially focused upon portions 402, 404, and 406, each of the portions 402, 404, and 406 may receive one or more HIFU pulses before the HIFU wave is directed to another portion of the object 400.

Figure 5:
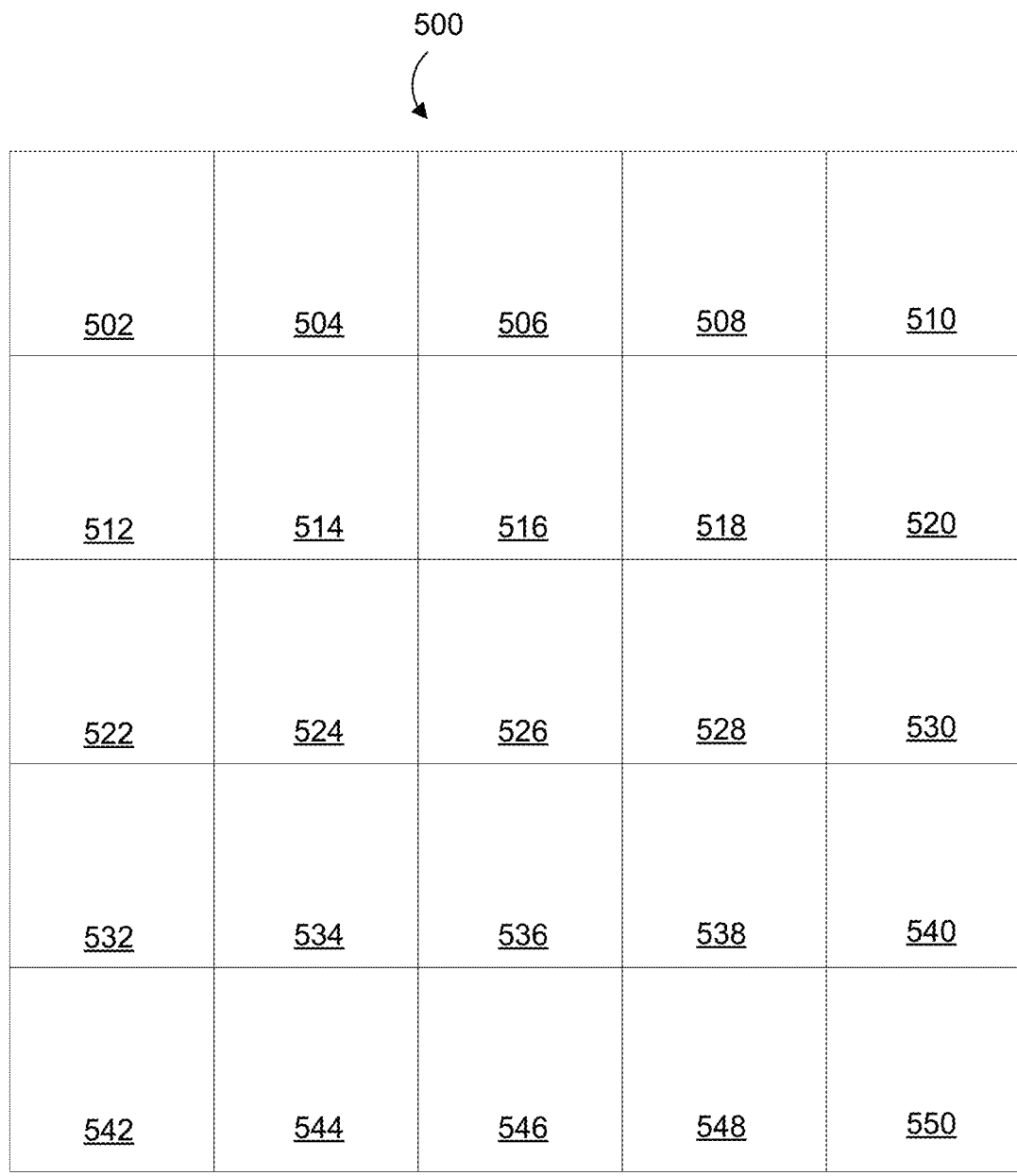
FIG. 5 depicts an array of distinct portions of an example object.

FIG. 5 depicts an example object 500 for the purpose of illustrating other example sequences or trajectories that a focal point of a HIFU wave could be directed along. A first example trajectory could include sequentially focusing the focal point upon horizontal portions of the object. Such an example trajectory is depicted as the sequence 502, 504, 506, 508, 510, 512, 514, 516, 518, 520, 522, 524, 526, 528, 530, 532, 534, 536, 538, 540, 542, 544, 546, 548, and 550. Another trajectory could include sequentially directing the focal point of the HIFU wave upon the portions of the object as defined by the sequence 502, 506, 510, 514, 518, 522, 526, 530, 534, 538, 542, 546, 550, 504, 508, 512, 516, 520, 524, 528, 532, 536, 540, 544, and 548. Yet another trajectory could include a spiral-like sequence 502, 504, 506, 508, 510, 520, 530, 540, 550, 548, 546, 544, 542, 532, 522, 512, 514, 516, 518, 528, 538, 536, 534, 524, and 526.

Numerous other trajectories or sequences are also possible. For example, the distinct portions of the object may form a closed loop, one or more concentric spheres, or one or more concentric circles. The distinct portions may all lie within a common line and/or a common plane. That is to say that the distinct portions of the object may define a line, an area, or a volume.

In some examples, the method 200 may further involve determining a trajectory of the distinct portions of the object such that distances between successive portions of the trajectory are maximized. In this context, sequentially directing the focal point upon the distinct portions of the object may include directing the focal point upon the distinct portions of the object according to the determined trajectory.

As a further example, an image captured by the sensor module 108 may be used to determine the trajectory. In this context, the method 200 may further involve capturing an image of the object, determining a trajectory of the distinct portions of the object based on the captured image, and sequentially directing the focal point upon the distinct portions of the object according to the trajectory determined based on the captured image.

By further example, it may be possible to determine the shape, size, location, and/or consistency of the object 500 based on a captured image of the object 500. Then, the trajectory could be determined to be any of the trajectories discussed above with reference to FIG. 5. For example, the ablation system may compare a known size of the focal point of the HIFU wave to the overall size of the object determined based on the captured image. The object may be divided into distinct portions that are all roughly the size of the focal point of the HIFU wave and the trajectory may be determined based on the division of the object into the distinct portions comparable in size to the focal point.

Sequentially directing the focal point upon the distinct portions of the object may also include determining how many pulses of the HIFU wave a given portion of the object should absorb before the focal point is redirected to another portion of the object. For example, the given portion may receive a number of pulses greater than 5 and less than about 200. More specifically, the given number of pulses may be about 30. The given number of pulses may roughly represent a number of pulses of the HIFU wave sufficient for effective ablation of the given portion, where the HIFU wave is defined by a given frequency, pulse duration, and shock amplitude. For example, a first portion may receive a certain number of HIFU pulses, fully ablating the first portion, and then the focal point of the HIFU wave may be redirected to a second portion so that the second portion may be ablated.

In other examples, the given number of pulses with appropriate duty cycle might not be provided to the first portion all in one continuous session. That is, the focal point of the HIFU wave may be directed upon the first portion for receiving only a portion of a predetermined number of pulses, then directed upon a second portion for receiving some or all of the predetermined number of HIFU pulses, and then redirected back to the first portion for receiving the remainder of the predetermined number of HIFU pulses.

At block 206, the method 200 involves, via the respective shock waves, causing the distinct portions of the object to boil and form respective vapor cavities. Referring to FIG. 4A, the HIFU wave 401 may experience non-linear propagation through the object 400 and become a shock wave near the center of portion 402, which in turn causes boiling within the portion 402. For example, a given volume of the portion 402 may be heated to at least 100° C. The given volume may be greater than 0.1 mm$^3$ and less than 0.5 mm$^3$. The boiling causes a vapor cavity 403 to be formed within the portion 402. In some examples, the volume of the vapor cavity 403 may be greater than about 3 cubic millimeters (mm$^3$) and less than about 30 mm$^3$. Generally, the portion 402 assumes a vapor state within the vapor cavity 403 and a liquid or solid form outside of the vapor cavity 403.

FIG. 4B depicts the HIFU wave 401 forming a shock wave near the center of portion 404, which in turn causes boiling within the portion 404. For example, a given volume of the portion 404 may be heated to at least 100° C. The given volume may be greater than 0.1 mm$^3$ and less than 0.5 mm$^3$. The boiling causes a vapor cavity 405 to be formed within the portion 404. In some examples, the volume of the vapor cavity 405 may be greater than about 10 mm$^3$ and less than about 30 mm$^3$. Generally, the portion 404 assumes a vapor state within the vapor cavity 405 and a liquid or solid form outside of the vapor cavity 405. FIG. 4B depicts portion 402 as an ablated void within the object 400. This will be discussed further below.

In a similar fashion, FIG. 4C depicts the HIFU wave 401 forming a shock wave near the center of portion 406, which in turn causes boiling within the portion 406. For example, a given volume of the portion 406 may be heated to at least 100° C. The given volume may be greater than 0.1 mm$^3$ and less than 0.5 mm$^3$. The boiling causes a vapor cavity 407 to be formed within the portion 406. In some examples, the volume of the vapor cavity 407 may be greater than about 10 mm$^3$ and less than about 30 mm$^3$. Generally, the portion 406 assumes a vapor state within the vapor cavity 407 and a liquid or solid form outside of the vapor cavity 407. FIG. 4C depicts portion 404 as an ablated void within the object 400. This will be discussed further below.

At block 208, the method 200 involves causing substantially uniform ablation of a region of the object that comprises the distinct portions. The substantially uniform ablation is caused via interaction of the respective shock waves with the respective vapor cavities. In some examples the ablated region of the object has a volume greater than about 1 cm$^3$ and less than about 10 cm$^3$.

As shown in FIGS. 4A and 4B, interaction of the vapor cavity 403 and the shock wave induced by HIFU wave 401 has ablated portion 402 of the object 400. For example, superheated vapor of the vapor cavity 403 provides a force pushing outward toward the remainder of the portion 402. This explosive boiling activity and interaction of shock waves with the vapor cavity 403 emulsifies the portion 402 to form a liquid-filled lesion devoid of cellular structure, with little to no thermal coagulation within the treated region. Portions 404 and 406 are similarly ablated by interaction of shock waves with respective vapor cavities 405 and 407, forming a uniformly ablated area or volume together with portion 402.

In some examples, both portions 402, 404, and 406 are liquefied within the object 400 to create a liquefied volume. Each time the HIFU wave 401 is focused upon a new portion of the object, the HIFU wave may cause a new liquefied volume to form within the new portion of the object. Such a liquefied volume may be greater than about 10 cubic mm$^3$ and less than about 30 mm$^3$. Alternatively, the focal point of the HIFU wave 401 may be directed upon various portions of the object to gradually form a large liquefied lesion across the region that includes the individual portions of the object.

In some examples, boiling of the respective portions of the object 400 may cause purely mechanical ablation (liquefaction), or mechanical ablation with some degree of thermal ablation of various portions of the object. Use of preferred parameters for the HIFU wave, however, will generally result in ablation that is primarily mechanical in nature and not thermal in nature. In examples where the object 400 is undesirable biological tissue, liquefied portions of the undesirable biological tissue may be flushed out of a human subject's body naturally through urination, or via their lymphatic and/or cardiovascular system, or taken out using a needle, for example.

Where the biological tissue is a tumor, the method may involve treating a subject having the tumor with an amount effective of the focused acoustic ultrasound wave to ablate all or a portion of the tumor.

Where the biological tissue is a hematoma, the method may involve treating a subject having the hematoma with an amount effective of the focused acoustic ultrasound wave to ablate all or a portion of the hematoma.

Where the biological tissue is an abscess, the method may involve treating a subject having the abscess with an amount effective of the focused acoustic ultrasound wave to ablate all or a portion of the abscess.

Where the biological tissue is a lipoma, the method may involve treating a subject having the lipoma with an amount effective of the focused acoustic ultrasound wave to ablate all or a portion of the lipoma.

Where the biological tissue is a diseased tissue, the method may involve treating a subject having the diseased tissue with an amount effective of the focused acoustic ultrasound wave to ablate all or a portion of the diseased tissue.

Wherein the biological tissue is a liver tissue, the method may involve treating a subject having the liver tissue with an amount effective of the focused acoustic ultrasound wave to ablate all or a portion of the liver tissue.

Where the biological tissue is a kidney tissue, the method may involve treating a subject having the kidney tissue with an amount effective of the focused acoustic ultrasound wave to ablate all or a portion of the kidney tissue.

Where the biological tissue is a muscle tissue, the method may involve treating a subject having the muscle tissue with an amount effective of the focused acoustic ultrasound wave to ablate all or a portion of the muscle tissue.

Where the biological tissue is a fat tissue, the method may involve treating a subject having the fat tissue with an amount effective of the focused acoustic ultrasound wave to ablate all or a portion of the fat tissue.

Where the biological tissue is a connective tissue, the method may involve treating a subject having the connective tissue with an amount effective of the focused acoustic ultrasound wave to ablate all or a portion of the connective tissue.

Where the biological tissue is an undesirable tissue, the method may involve treating a subject having the undesirable tissue with an amount effective of the focused acoustic ultrasound wave to ablate all or a portion of the undesirable tissue.

Where the biological tissue is a brain tissue, the method may involve treating a subject having the brain tissue with an amount effective of the focused acoustic ultrasound wave to ablate all or a portion of the brain tissue.

Where the biological tissue is a nerve tissue, the method may involve treating a subject having the nerve tissue with an amount effective of the focused acoustic ultrasound wave to ablate all or a portion of the nerve tissue.

To further clarify aspects of this disclosure, experimental procedures and results involving the use of the disclosed methods and systems will be discussed below.

FIG. 6 depicts pressure waveforms generated within a test medium of water. A Sonalleve 3.0 T Philips Healthcare magnetic resonance (MR)-guided HIFU system was used to generate shock waves at a focal point in water. The HIFU transducer in a form of a multi-element phased array was configured as follows: a 128 mm shell diameter, a 120 mm focus, and 256 transducer elements each having a 6.6 mm diameter. The system was operated to generate HIFU waves at an oscillation frequency of 1.2 MHz at operating powers of 250 W and 600 W. At 250 W, the system generated a maximum pressure of 79 MPa within the water and a minimum pressure of −11.8 MPa within the water, resulting in a shock wave amplitude of 75 MPa. At 600 W, the system generated a maximum pressure of 96 MPa within the water and a minimum pressure of −17.3 MPa within the water, resulting in a shock wave amplitude of 110 MPa.

Figure 7:
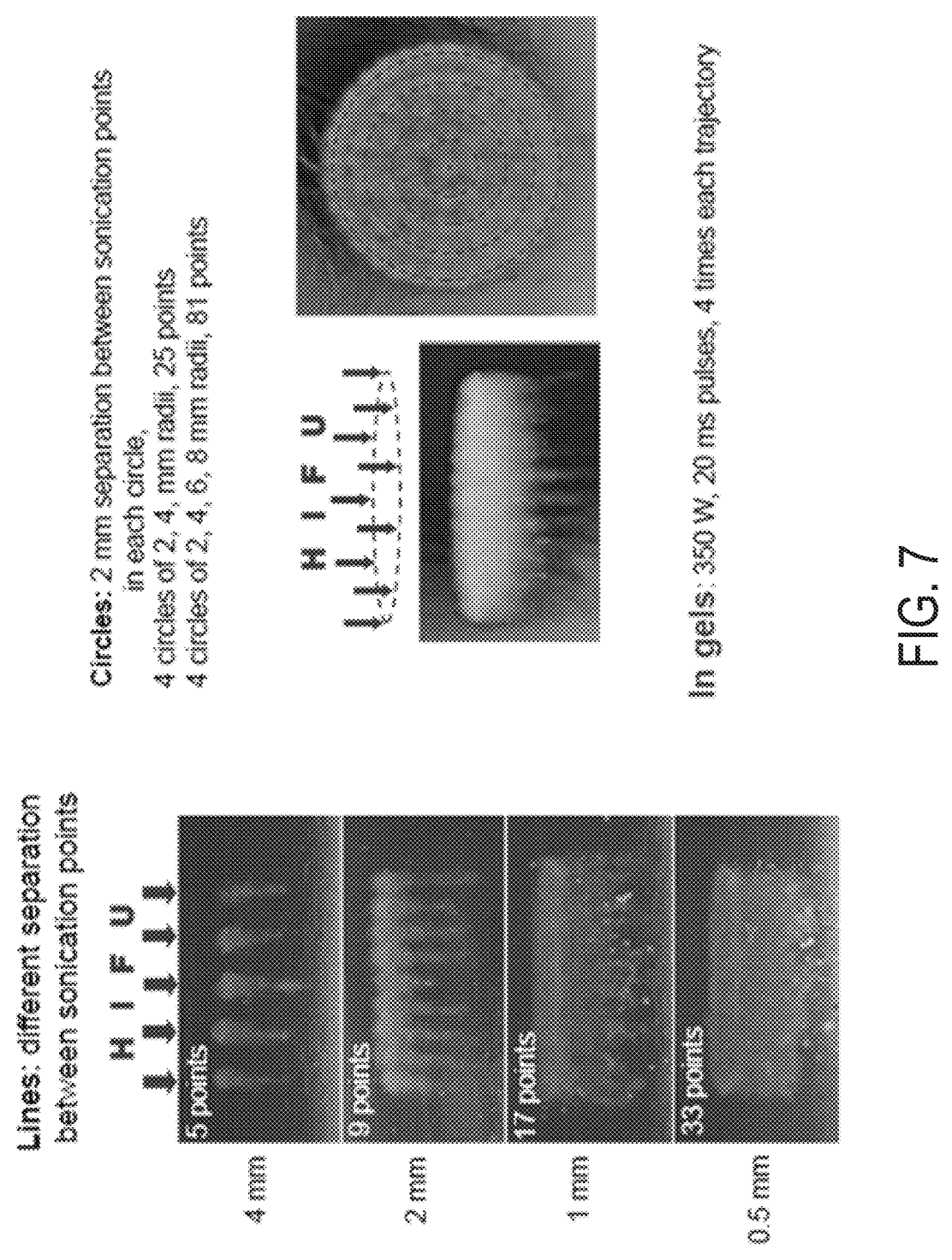

FIG. 7 depicts example ablation trajectories within a test medium, namely polyacrylamide gel. The parameters of the HIFU waves used to ablate the gel included an operating power of 350 W and 20 ms pulse duration. All points of the trajectories depicted in FIG. 7 absorbed four HIFU pulses. Two sets of example trajectories ablated within the gel are shown in FIG. 7.

Depicted at the left of FIG. 7, the example system was shown to be capable of generating ablated lines within the gel each comprising several ablation points. A first line included 5 collinear points separated by respective distances of 4 mm, a second line included 9 collinear points separated by respective distances of 2 mm, a third line included 17 collinear points separated by respective distances of 1 mm, and a fourth line included 33 collinear points separated by respective distances of 0.5 mm.

Depicted at the right of FIG. 7, another ablation trajectory included 4 concentric circles: a first circle of radius 2 mm comprised of 8 points equally spaced along the circumference of the first circle, a second circle of radius 4 mm comprised of 16 points equally spaced along the circumference of the second circle, a third circle of radius 6 mm comprised of 24 points equally spaced along the circumference of the third circle, and a fourth circle of radius 8 mm comprised of 32 points equally spaced along the circumference of the fourth circle. A common center point was also ablated at the center of the four concentric circles.

In another example (not shown in FIG. 7), excised bovine liver tissue was ablated according to the following parameters: an ablation depth of 2 cm from the surface of the tissue, a pulse duration range of 10-15 ms, a pulse repetition frequency range of 1-10 Hz, 250 W power, a shock amplitude of 75 MPa, and a 30-pulse dose per ablation point. Two ablation layers separated by a depth of 5 mm were generated within the tissue. A first layer included a first ablated circle of radius 2 mm comprising 8 ablation points and a second circle of radius 4 mm comprising 16 ablation points, as well as an ablation point coinciding with the center of the first and second circles. The second layer included a third ablated circle of radius 2 mm comprising 8 ablation points and a fourth circle of radius 4 mm comprising 16 ablation points, as well as an ablation point coinciding with the center of the third and fourth circles. The third circle was essentially a reproduction of the first circle at a decreased depth within the tissue and the fourth circle was essentially a reproduction of the second circle at an decreased depth within the tissue.

Figure 8:
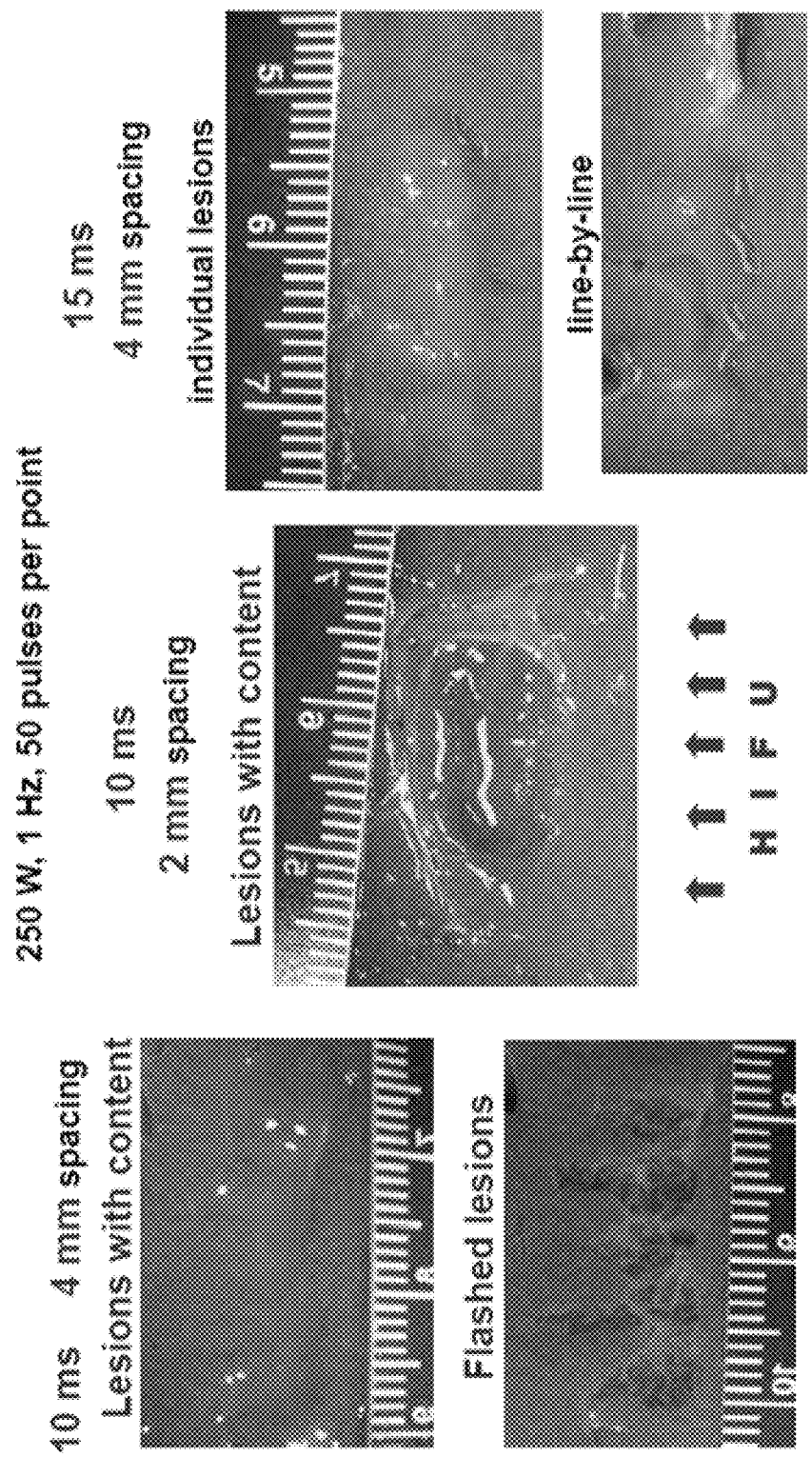
FIG. 8 depicts mechanically ablated lines within ex-vivo bovine liver tissue.

FIG. 8 depicts ablated lines within ex-vivo bovine liver tissue. Five ablated portions of the tissue that form a line are depicted at the left of FIG. 8. The five lesions were spaced at 4 mm and were ablated at an operating power of 250 W, a pulse repetition frequency of 1 Hz, and a 10 ms pulse duration (for a corresponding duty cycle of 1%). Each lesion absorbed 50 pulses. The image captioned "Lesions with content" shows ablated tissue that remained within cavities formed via the ablation process. The image captioned "Flashed lesions" shows the cavities after the ablated tissue was rinsed with water. At a spacing of 4 mm, the lesions appeared to merge together as shown at the bottom end of the respective images.

A series of ablated portions of the tissue that are spaced at 2 mm are depicted at the center of FIG. 8. At this spacing, the ablated portions essentially overlapped into a continuous region. The series of legions were ablated at an operating power of 250 W, a pulse repetition frequency of 1 Hz, and a 10 ms pulse duration (for a corresponding duty cycle of 1%).

A series of ablated portions of the tissue that were spaced at 4 mm are depicted in the image captioned "individual lesions" at the top right of FIG. 8. The series of lesions were ablated at an operating power of 250 W, a pulse repetition frequency of 1 Hz, and a 15 ms pulse duration (for a corresponding duty cycle of 1.5%).

FIG. 9 depicts additional ablated ex-vivo bovine liver tissue. 33 portions of the tissue spaced at 0.5 mm were ablated with an operating power of 300 W and a pulse repetition frequency of 1 Hz. Each portion received 8 pulses. The image captioned "Axial cross—section" shows each mechanically ablated portion having a thermally damaged narrow tail of approximately 100 µm in width.

Figure 10:
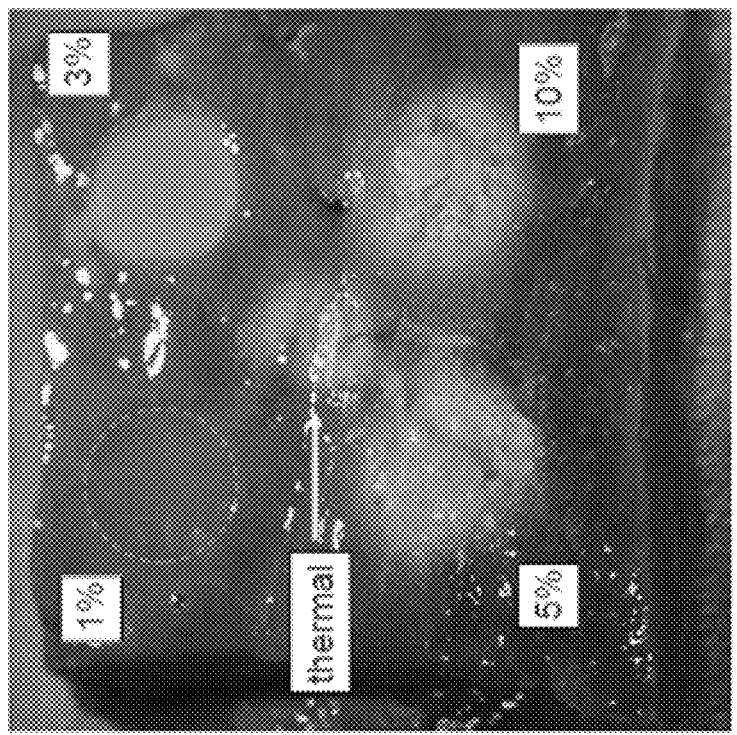
FIG. 10 depicts ablated portions of ex-vivo bovine liver that correspond to concentric circle trajectories and differing ablation duty cycles.

FIG. 10 depicts ablated portions of ex-vivo bovine liver that correspond to differing ablation duty cycles. The lesions shown in FIG. 10 were formed with the following HIFU parameters: 250 W operating power, 10 ms pulse duration, and 30 pulses per ablation point. Two layers separated by 5 mm of tissue depth were ablated for each lesion shown. At a duty cycle of 1% the ablated portion of tissue was mechanically ablated, but had an appearance very similar to that of non-ablated portions of the tissue, indicating a substantial lack of thermal effects in the ablated portion. At a duty cycle of 3%, some thermal effect was seen, but the ablated area was substantially the same as the area that actually absorbed the HIFU wave. At a duty cycle of 5%, thermal effects were more prominent but the ablated area did not extend beyond the area that actually absorbed the HIFU wave. At a duty cycle of 10%, the thermal effects were even more prominent but still the ablated area almost coincided with the area that absorbed the HIFU wave.

FIG. 11 depicts additional ablation of liver tissue. As a general matter, it is shown that connective tissue embedded within the liver tissue was resistant to being ablated by the HIFU waves. The liver sample depicted in FIG. 11 was irradiated at an operating power of 250 W. The images on the left side of FIG. 11 depict ablation of a circular region of liver tissue having a 2 cm diameter at a duty cycle of 5%. This region was ablated via sequential ablation of 81 points lying on 4 concentric circles of varying diameter. Each point absorbed 25 pulses of the HIFU wave.

The images on the right side of FIG. 11 depict ablation of circular regions of the ex-vivo bovine liver sample having diameters of 1 cm at duty cycles of 1% and 3%. These regions were ablated via sequential ablation of 25 points lying on 2 concentric circles of varying diameter. These circles were ablated at two different depths within the tissue separated by 5 mm. Each ablated point absorbed 30 pulses of the HIFU wave. As shown, thermal effects were not apparent in the lesion generated at 1% duty cycle but were slightly noticeable at 3% duty cycle. Notwithstanding the noticeable thermal effect, at 3% duty cycle the ablated region and the region that absorbed the HIFU wave largely coincided.

Figure 12:
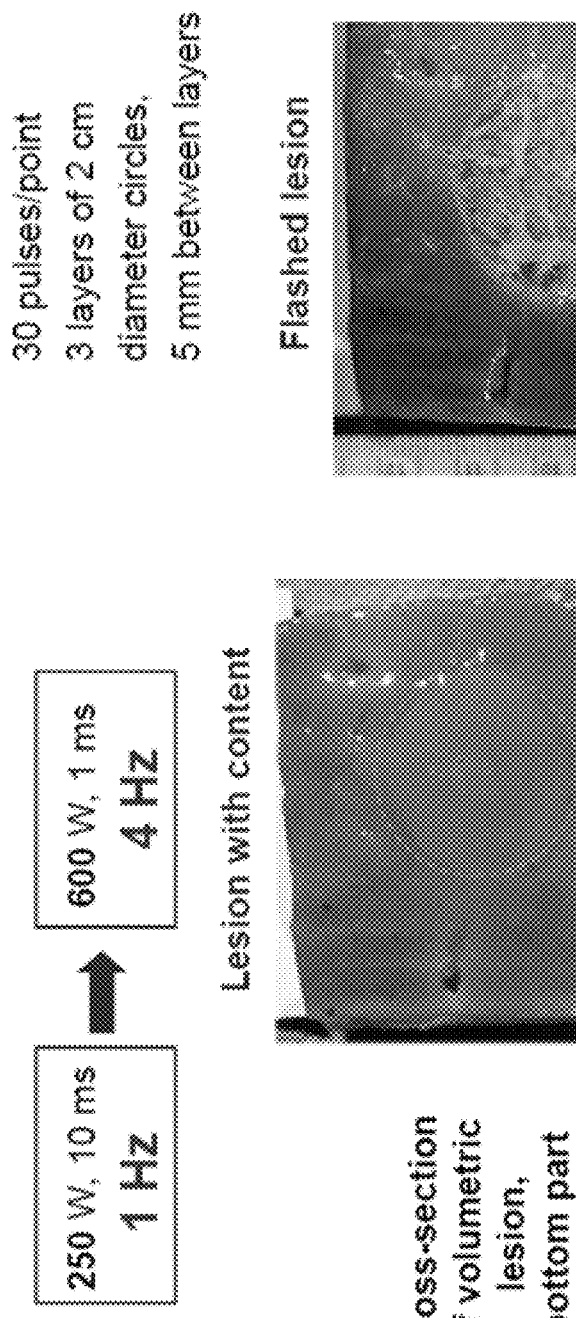
FIG. 12 depicts ablation of tissue at varying power, shock amplitude at the shock wave focus, pulse duration, and pulse repetition frequency.

FIG. 12 depicts ablation of tissue at increased power and pulse repetition frequency. Tissues depicted in FIG. 12 were ablated at an operating power of 600 W, 110 MPa shock front, a 1 ms pulse duration, and a pulse repetition frequency of 4 Hz. Three circles having 2 cm diameters were respectively ablated on three layers of the tissue separated by depths of 5 mm. Using these HIFU parameters, suitable ablation of tissue was accomplished four times faster than ablation performed at an operating power of 250 W, 75 MPa shock front, a 10 ms pulse duration, and a 1 Hz pulse repetition frequency.

Figure 13:
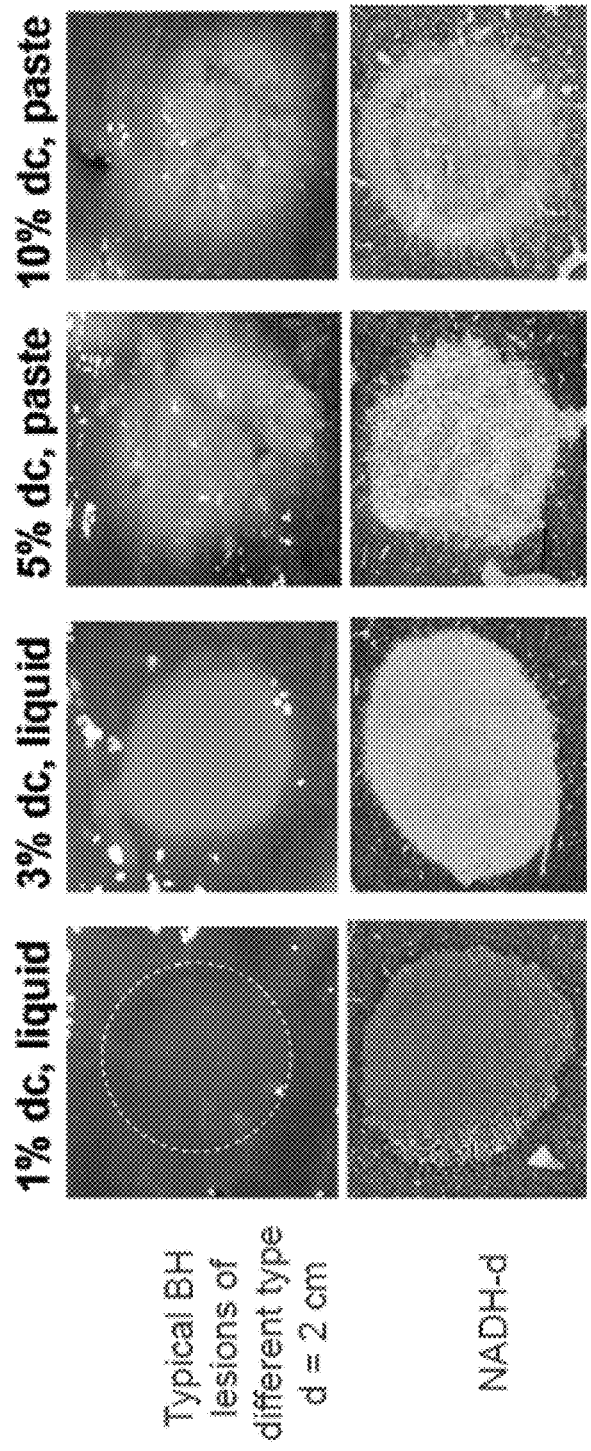
FIG. 13 depicts ablated tissue portions and histological slides corresponding to differing ablation duty cycles.

FIG. 13 depicts ablated tissue portions corresponding to differing ablation duty cycles. As shown, an increase in duty cycle correlated with increased thermal effect within the ablated tissue. Tissue ablated via HIFU formed a paste instead of being liquefied if thermal effects were too extensive. Also notable was that the ablated portion of the tissue only slightly expanded beyond the boundary of the region that actually absorbed the HIFU wave as the duty cycle is increased.

While various example aspects and example embodiments have been disclosed herein, other aspects and embodiments will be apparent to those skilled in the art. The various example aspects and example embodiments disclosed herein are for purposes of illustration and are not intended to be limiting, with the true scope and spirit being indicated by the following claims.

The invention claimed is:

1. A method comprising:
 determining a trajectory based on characteristics of an object in tissue and a size of a focal point associated with an ultrasound transducer array, the trajectory including a first layer and a second layer set at different depths in the tissue;
 generating, using the ultrasound transducer array, an acoustic ultrasound wave that is focused at the focal point;
 directing the focal point upon a first portion of the object in the first layer to form first shock waves at the first portion, thereby applying a first ultrasound dose to the first portion and causing the first portion to boil and form a first vapor cavity via the first shock waves, wherein the first ultrasound dose is defined by a first quantity of first ultrasound pulses, a first amplitude of the first shock waves, a first oscillation frequency of the first ultrasound pulses, a first pulse duration of the first ultrasound pulses, and a first duty cycle of the first ultrasound pulses, and a first pulse repetition frequency that is greater than or equal to 4 Hz and less than or equal to 15 Hz; and
 directing the focal point upon each second portion of a plurality of second portions of the object according to the trajectory in which the focal point is sequentially directed among second portions that are adjacent to second portions, to form second shock waves at each second portion of the plurality, thereby applying a second ultrasound dose to each second portion of the plurality, wherein at least one second portion of the plurality of second portions is in the second layer, wherein the second ultrasound dose is defined by a second quantity of second ultrasound pulses that is substantially equal to the first quantity, a second amplitude of the second shock waves that is substantially equal to the first amplitude, a second pulse duration that is substantially equal to the first pulse duration, a second oscillation frequency that is substantially equal to the first oscillation frequency, a second duty cycle that is substantially equal to the first duty cycle, and a second pulse repetition frequency that is substantially equal to the first pulse repetition frequency, and causing each second portion of the plurality to boil and form a second vapor cavity via the second shock waves, wherein the plurality of second portions are distinct from each other and from the first portion.

2. The method of claim 1, wherein the tissue is a biological object tissue within a living organism.

3. The method of claim 2, wherein the biological tissue is selected from a group consisting of a brain tissue, a nerve tissue, a liver tissue, a kidney tissue, a muscle tissue, a fat tissue, a connective tissue, a tumor, a hematoma, an abscess, a lipoma, a diseased tissue, and an undesirable tissue.

4. The method of claim 1, wherein the first oscillation frequency is greater than 900 kHz and less than 20 MHz.

5. The method of claim 1, wherein the first pulse duration is greater than 0.1 millisecond and less than or equal to 40 milliseconds.

6. The method of claim 1, wherein the first quantity is greater than 5 and less than about 200.

7. The method of claim 1, wherein the first portion and the plurality of second portions are not colinear and/or not coplanar.

8. The method of claim 7, wherein the first portion and the plurality of second portions form one or more concentric circles and/or one or more concentric spheres.

9. The method of claim 1, wherein causing the first portion of the object to boil and form the first vapor cavity comprises heating the first portion to at least 100° C.

10. The method of claim 1, wherein determining the trajectory comprises:
capturing an image of the object; and
determining the trajectory that includes the first portion and the plurality of second portions based on the image, wherein the focal point is directed upon the first portion and the plurality of second portions according to the trajectory determined based on the image.

11. The method of claim 10, the method further comprising:
determining the size, a shape, or a location of the object based on the image; and
apportioning the object into the first portion and the plurality of second portions based on the size, the shape, or the location.

12. The method of claim 1, further comprising:
receiving input representing one or more parameters for generating the acoustic ultrasound wave or directing the focal point,
wherein the acoustic ultrasound wave is generated and/or directed according to the input.

13. A non-transitory computer-readable medium storing instructions that, when executed by an ablation system, cause the ablation system to perform the method of claim 1.

14. The method of claim 1, wherein applying the first ultrasound dose to the first portion and applying the second ultrasound dose to the plurality of second portions comprises causing substantially uniform ablation of the first portion and the plurality of second portions.

15. The method of claim 14, wherein causing the substantially uniform ablation of the first portion and the plurality of second portions comprises causing mechanical ablation of the first portion and the plurality of second portions.

16. An ablation system configured to ablate an object, the ablation system comprising:
one or more processors;
a sensor module configured to collect sensory data from the object during ablation;
an input/output interface configured to receive user input and display an image representing the sensory data;
an ablation module configured to generate an acoustic ultrasound wave and sequentially direct a focal point of the acoustic ultrasound wave upon distinct portions of the object; and
a non-transitory computer-readable medium storing instructions that, when executed by the one or more processors, cause the ablation system to perform the method of claim 1.

17. The method of claim 1, wherein directing the focal point comprises directing the focal point via electronic steering of an array of transducer elements.

18. The method of claim 1, wherein the first amplitude is at least 40 MPa, wherein the first duty cycle is greater than 0.5% and less than 12%, wherein a volume of the first portion is greater than 0.1 mm$^3$ and less than 0.5 mm$^3$, wherein a volume of each second portion of the plurality is greater than 0.1 mm$^3$ and less than 0.5 mm$^3$, and wherein a total volume of the first portion and the plurality of second portions is at least 1 cm$^3$.

19. The method of claim 1, wherein determining the trajectory comprises dividing the object into a plurality of distinct portions comparable in size to the focal point.

20. The method of claim 1, wherein the first layer and the second layer are separated by about 5 mm.

21. The method of claim 1, wherein the first layer defines a first pattern and the second layer defines a second pattern, wherein the second pattern is different than the first pattern.

* * * * *